US007459276B2

(12) United States Patent
Cantor et al.

(10) Patent No.: US 7,459,276 B2

(45) Date of Patent: Dec. 2, 2008

(54) METHODS AND CONTROLS FOR MONITORING ASSAY QUALITY AND ACCURACY IN PARATHYROID HORMONE MEASUREMENT

(75) Inventors: Thomas L. Cantor, El Cajon, CA (US); Ping Gao, San Diego, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 600 days.

(21) Appl. No.: 10/674,294

(22) Filed: Sep. 29, 2003

(65) Prior Publication Data

US 2005/0069952 A1 Mar. 31, 2005

(51) Int. Cl.
*G01N 33/53* (2006.01)

(52) U.S. Cl. ........................ 435/7.1; 435/7.2; 435/7.91; 435/7.92; 435/7.94

(58) Field of Classification Search .................. 435/7.1, 435/7.92, 7.93, 7.94
See application file for complete search history.

(56) References Cited

U.S. PATENT DOCUMENTS

| | | | | |
|---|---|---|---|---|
| 5,496,801 | A * | 3/1996 | Holthuis et al. | 514/12 |
| 6,387,711 | B1 | 5/2002 | Sundaram et al. | 436/534 |

OTHER PUBLICATIONS

Bouillon et al.. Clin. Chem. (1990) vol. 36, p. 271-276.*
Geysen et al. J. Mol Recognition 1998, vol. 1, p. 32-40.*
Lerner et al. Nature 1982, vol. 299, p. 592-596.*
Gao et al., J. Bone Miner Res. 16(4):605-615 (2001).
Monier-Faugere et al., Kidney International 60:1460-1468 (2001).
Woodhead, Clin. Biochem. 23:17 (1990).

* cited by examiner

*Primary Examiner*—Long V. Le
*Assistant Examiner*—Changhwa J Cheu
(74) *Attorney, Agent, or Firm*—Morrison & Foerster LLP

(57) ABSTRACT

The present invention relates to the use of control compositions and kits comprising such to evaluate and monitor the consistency of assays utilized to determine parathyroid hormone levels.

15 Claims, 2 Drawing Sheets

Whole Human PTH (1-84)

METHODS AND CONTROLS FOR MONITORING ASSAY QUALITY AND ACCURACY IN PARATHYROID HORMONE MEASUREMENT

TECHNICAL FIELD

The present invention relates to the use of control compositions and kits comprising such to evaluate and monitor the consistency of assays utilized to determine parathyroid hormone levels.

BACKGROUND ART

Calcium plays an indispensable role in cell permeability, the formation of bones and teeth, blood coagulation, transmission of nerve impulse, and normal muscle contraction. The concentration of calcium ions in the blood is, along with calcitrol and calcitonin, regulated mainly by parathyroid hormone (PTH). Although calcium intake and excretion may vary, PTH serves through a feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

The complete form of human PTH, sometimes referred to in the art as hPTH but referred to in the present invention as an example of PTH agonist, is a unique 84 amino acid peptide (SEQ ID NO:1), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism. Researchers have also found that a large circulating PTH fragment (e.g., cyclase inactive parathyroid hormone) functions as a naturally occurring PTH antagonist. Cyclase inactive PTH has been found to be useful, alongside whole PTH, as an indicator in separating untreated end stage renal disease (ESRD) patients with high bone turnover from those with adynamic low bone turnover. (See Faugere, M. C. et al., Kidney International 2001; 60: 1460-1468.)

The clinical need for accurate measurement of PTH is well demonstrated. Serum PTH level is one of the most important indices for patients with the following diseases: familial hypocalciuria; hypercalcemia; multiple endocrine neoplasia types I and II; osteoporosis; Paget's bone disease; primary hyperparathyroidism-caused by primary hyperplasia or adenoma of the parathyroid glands; pseudohypoparathyroidism; and renal failure, which can cause secondary hyperparathyroidism.

Determining circulating biologically active PTH levels in humans has been challenging. One major problem is that PTH is found at low levels, normally 10 pg/mL to 65 pg/mL. Coupled with extremely low circulating levels is the problem of the heterogeneity of PTH and its many circulating fragments. In many cases, immunoassays have faced substantial and significant interference from circulating PTH fragments. For example, some commercially available PTH kits have almost 100% cross-reactivity with the non-(1-84) PTH fragment.

Cross-reactivity of PTH immunoassay reagents and related interfering factors have resulted in inaccuracies in PTH level assessments. Frequently, those under tang PTH level assessments may not be aware of the discrepancies between actual and measured PTH levels in subjects. As the sensitivity of PTH assays is very important for treatment decisions in subjects, there is a need in the art for means to enable the assessment, monitoring, and adjusting of PTH assay results to obtain a reliable indicator of actual PTH levels in a subject. Such information would be useful to clinical labs and health care providers in terms of risk assessment and risk management related issues. Moreover, there is a need in the art for control compositions that maintain an extended shelf life. The present compositions, methods and kits address these and other needs in the art.

DISCLOSURE OF THE INVENTION

The present invention relates to methods of, and products for, calibrating hormone assays, and monitoring the consistent performance of, particularly PTH assays, which can provide a more accurate assay system having minimal assay variation.

In one embodiment parathyroid hormone (PTH) assay controls are provided comprising a composition having a known concentration of PTH components comprising a whole PTH component having an amino acid sequence set forth in SEQ ID NO:1 ($PTH_{1-84}$), wherein the N-terminal amino acid residue of the PTH molecule must be intact; and a PTH fragment component having an amino acid sequence set forth in SEQ ID NO:1 ($PTH_{1-84}$), wherein the N-terminal amino acid residue of the PTH fragment starts at any position spanning position 2 through position 33 of the $PTH_{1-84}$, the C-terminal amino acid residue of the PTH fragment ends at any position spanning position 35 through position 84 of the $PTH_{1-84}$; and the PTH fragment has a minimal length of three amino acid residues. Frequently, the PTH fragment component comprises one or more different groupings of PTH fragments, each PTH fragment grouping having a distinct amino acid sequence. Also frequently the whole PTH component comprises $PTH_{1-84}$ and the PTH fragment component comprises $PTH_{7-84}$. Although human PTH is discussed extensively herein, PTH derived from other species having known amino acid sequence variations from human PTH are also contemplated.

Frequently, the presently disclosed controls further comprise a base composition comprising a protein matrix base. Also frequently, the present controls are comprised of a combination of a whole PTH and a PTH fragment component at a predetermined ratio. In one aspect, the concentration of the PTH components in the composition are measured or premeasured by measuring the amount of each individual component in the total composition. In another aspect, the present controls are frequently prepared such that the concentration of the individual PTH components in the control composition lies within a discreet physiological range. Frequently, the whole PTH component lies in a physiological range between about 0.7 pmol/L to about 3.9 pmol/L, or often between about 1 pmol/L to about 4 pmol/L. The presently described controls can be prepared and stored in a liquid or dry form. Frequently, when the controls are dried for storage, they are lyophilized. When the control compositions are dried and reconstituted for use, these compositions are generally reconstituted such that the concentration of the one or more individual components lies within a discreet physiological range. Often lyophilized controls of the present disclosure are reconstituted using a protein matrix.

Also frequently, the whole PTH component and/or the PTH fragment component comprise chemically synthesized PTH peptides. And, on occasion, the whole PTH component and/or the PTH fragment component are obtained as recombinant protein. Also frequently, the whole PTH component and/or the PTH fragment component are obtained from natural sources. In one aspect, natural sources of the PTH fragment and whole PTH components comprise human serum, human plasma, or a crude sample or extract of a human parathyroid gland. Frequently, the whole PTH component and/or the PTH fragment component are provided in a purified or neat form in a soluble protein matrix base, wherein the whole PTH component and/or the PTH fragment component are purified prior to incorporation within the protein matrix.

In another aspect, the present controls have extended shelf/storage lives. Accordingly, in one embodiment, the shelf-life of the present controls comprises a minimum of about 3 months. Often the controls have a shelf-life of about 3 months to about 1 year. Frequently, the shelf-life of the present controls is between about 2 to about 3 years. On occasion, the present controls have a shelf-life between about 3 months to about 10 years. Frequently, the present controls comprise a non-reconstituted PTH component that has a useful shelf life of at least three months at 4 degrees C. Also frequently, the present controls comprise a non-reconstituted PTH component that has a useful shelf life of up to about 10 years at 4 degrees C.

Frequently, the ratio of the whole PTH component to the PTH fragment component in the present controls lies within a discreet physiological range. On occasion, the ratio of the whole PTH component to the PTH fragment component in the present controls ranges between about 1% to about 99%. Frequently, the PTH fragment component or the whole PTH component ranges between about 20% to about 80% of the total PTH present in the composition. Moreover, frequently the ratio of the whole PTH component to the PTH fragment component in the control lies within a discrete range within the above ranges. In a related aspect, the ratio of the whole PTH component to the PTH fragment component in the control is a known and discrete ratio within the disclosed ratios ranging between about 1% to about 99%.

In another embodiment, kits are provided comprising one or more control compositions of the present disclosure, further including instructions therefore. In one aspect, the present diagnostic test kits comprise a plurality of standards of known percentages of whole PTH and/or PTH fragments in a solution comprising a protein matrix base. Frequently, when a plurality of standards are included in a kit, each of the one or more control compositions comprises a composition having a different known concentration of the PTH components. Also frequently, a plurality of standards may include one or more control compositions, each having a predetermined ratio of whole PTH to PTH fragment components. In a non-limiting example, each of the one or more controls may comprise a composition having a different known concentration of the combination of PTH components. Further, kits are provided wherein each of the one or more controls comprises a composition having a different predetermined ratio of the whole PTH component versus the PTH fragment component.

On occasion, the presently contemplated kits further comprise a solid phase coated with the whole PTH and/or PTH fragment antibody components or labeled whole PTH and/or labeled PTH fragment antibody components. In a further aspect of the invention, the PTH antibody component is labeled, e.g., acridities ester label. Other aspects contain other suitable labels such as particulate, fluorescent, enzymatic, colorimetric, dye, radioactive, magnetic or other such labels known in the art.

In a further embodiment, methods are provided to verify the accuracy of a PTH assay, comprising one or more trials of the following: a) evaluating a control of the type described herein utilizing a PTH assay having a specificity for a PTH component in the control; b) determining the concentration(s) of the PTH components in the composition utilizing the assay of step a); and c) comparing the results obtained in step b) with the known concentration(s) of the one or more components in the control or previously obtained values for the control; wherein the results of step c) are utilized to provide a basis for accepting, rejecting or interpreting PTH assay results obtained through the use of the PTH assay of step a) for non-control samples. Also frequently, the contemplated methods further comprise generating a standard deviation of the control results from previous assay trials after one or more trials in order to derive a basis for accepting or rejecting future assay runs. In a related aspect, step a) comprises evaluating the control by one or more PTH assays, each having a specificity for a different PTH component, or a combination of the PTH components, present in the control.

In a further embodiment, methods are provided to improve the accuracy of a PTH assay, comprising one or more trials of the following: a) evaluating a control of the type described herein utilizing a PTH assay having a specificity for a PTH component in the control, whereby each PTH component in the control is evaluated; b) determining the concentration of each of the PTH components and the ratio of PTH components in the control utilizing the assay of step a); and c) comparing the results obtained in step b) with the known concentration(s) and predetermined ratio of the components; wherein the results of step c) are utilized to modify or interpret PTH assay results obtained through the use of the PTH assay of step a) for non control samples. In a related aspect, step a) comprises evaluating the control by multiple PTH assays having different specificities and the concentration(s) of the one or more components are determined by combining the results of the multiple PTH assays.

In another embodiment, a method is provided to verify the accuracy of a PTH assay, comprising one or more trials of the following: a) evaluating a control containing a predetermined ratio of PTH components utilizing a PTH assay having a specificity for whole PTH and determining the concentration of whole PTH in the control; b) evaluating said control utilizing a PTH assay that detects whole PTH and PTH fragments and determining the concentration of the whole PTH and PTH fragment components in the control; c) determining the ratio of whole PTH versus PTH fragments by comparing the evaluation results of steps a) and b); d) comparing the results obtained in step c) with the predetermined ratio or previously obtained ratio of the control; wherein the results of step d) are utilized to modify or interpret PTH assay results obtained through the use of the PTH assays of steps a) and b) for non-control samples. Frequently, the results of step c) are utilized to modify or interpret PTH assay results obtained through the use of the PTH assay of step a) for non-control samples. Also frequently, the contemplated methods further comprise generating a standard deviation of the control results after one or more trials. In a related aspect, step a) comprises evaluating the control by multiple PTH assays having different specificities; and the concentration(s) of the PTH components are determined by combining the results of the multiple PTH assays. In another embodiment, the above methods are useful to adjust the accuracy of a PTH assay.

In another embodiment, a method is provided to verify the accuracy of a combination of PTH assays, comprising one or more trials of the following: a) evaluating a control of the type described herein utilizing a PTH assay having a specificity for whole PTH and determining the concentration of whole PTH in the control; b) evaluating said control utilizing a PTH assay that detects whole PTH and PTH fragments and determining the concentration of the whole PTH and PTH fragment in the control; c) determining the ratio of whole PTH to PTH fragments by comparing the concentration results of steps a) and b); and d) comparing the results obtained in step c) with the predetermined ratio of a control of the type discussed above; wherein the results of step d) are utilized to modify or interpret PTH assay results obtained through the use of the PTH assays of steps a) and b) for non-control samples. Frequently, the present method further comprises generating a standard deviation of the results of step c) versus the predetermined ratio after one or more trials. Also frequently, each of the one or more trials entails the evaluation of a different control having a different predetermined ratio. In one aspect, the PTH assay of step a) detects whole PTH having an intact N-terminal portion, and the PTH assay of step b) detects total PTH levels.

It will be apparent to one of ordinary skill in the art that specific embodiments of the present invention may be directed to one, some or all of the above-indicated aspects as well as other aspects, and may encompass one, some or all of the above- and below-indicated embodiments as well as other embodiments.

DETAILED DESCRIPTION OF PREFERRED EMBODIMENTS

Figure 1:
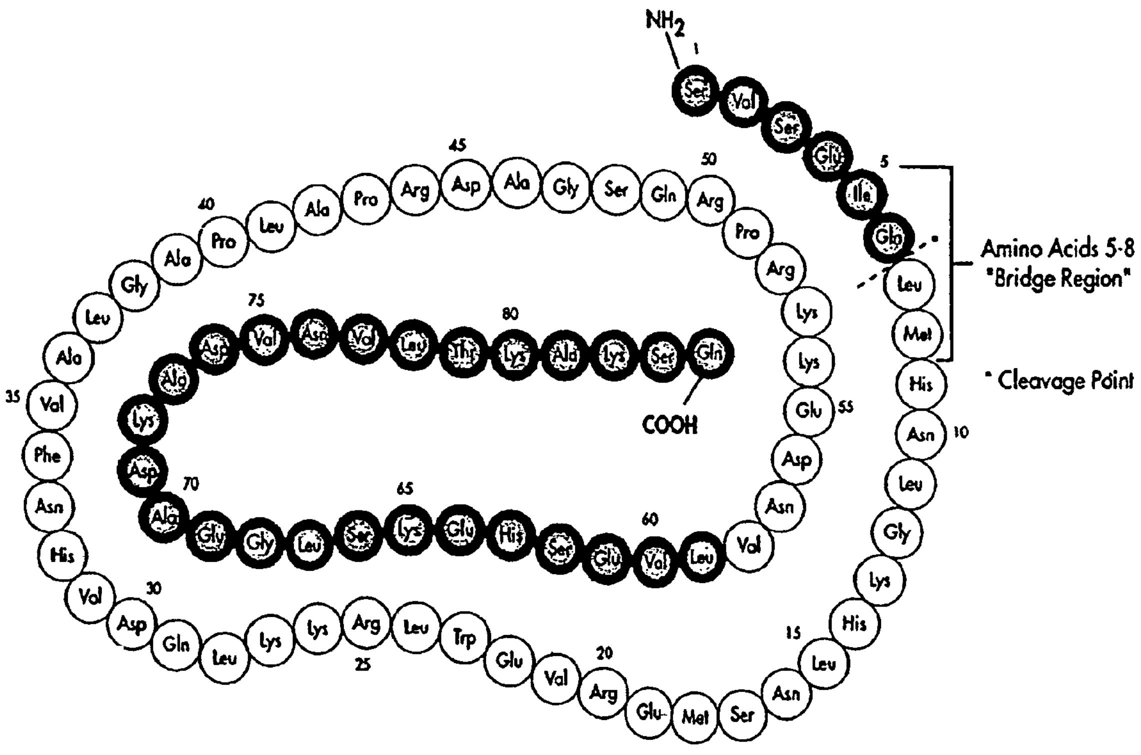
FIG. 1 is a diagrammatic view of human wPTH.
Figure 2:
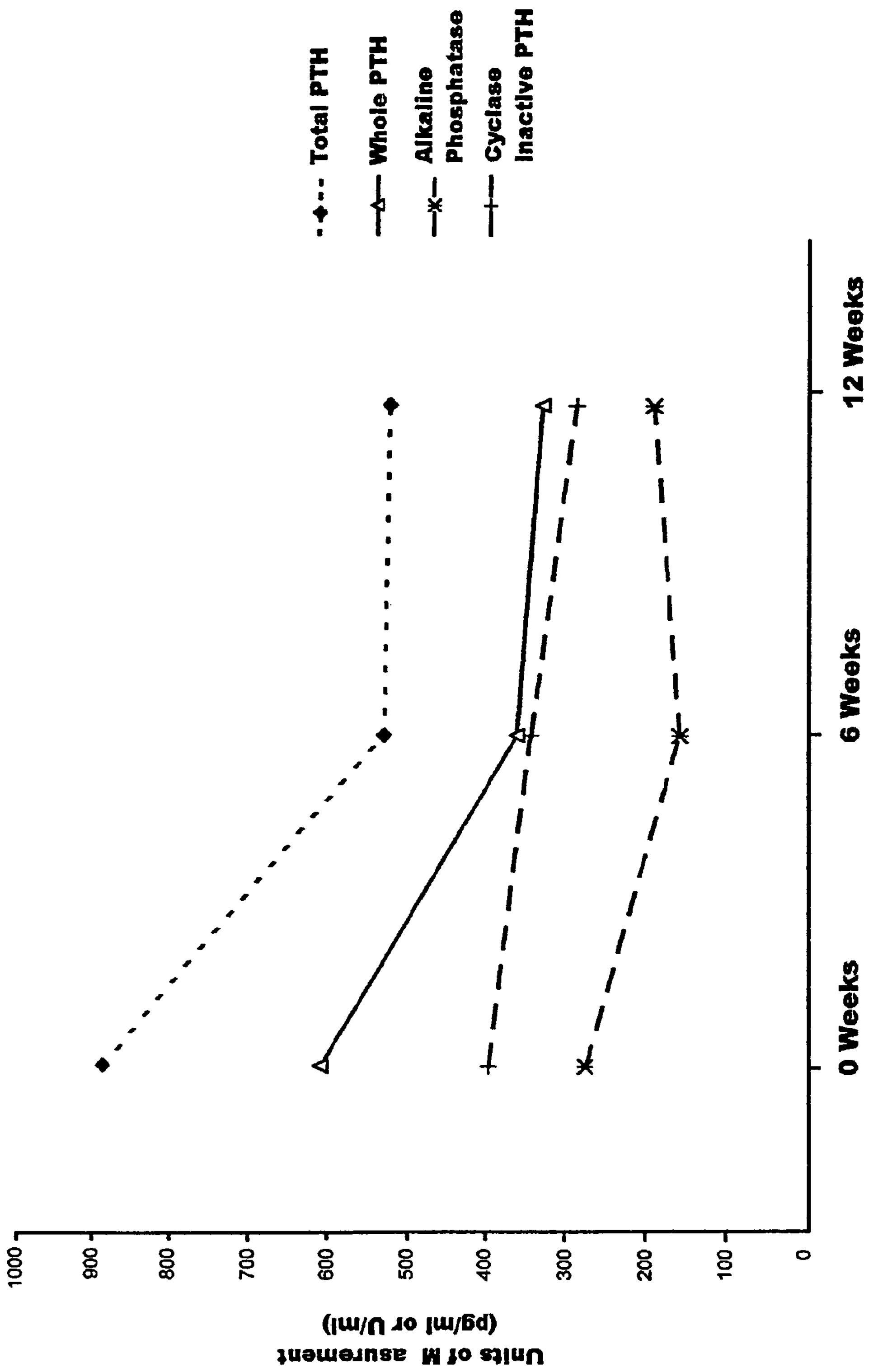
FIG. 2 is a graph comparing PTH measurement parameters over time for patients receiving a PTH suppressant therapy.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "whole parathyroid hormone (PTH)" refers to the complete molecule of PTH or a fragment, derivative or analog thereof that stimulates osteoclasts formation and bone turnover to increase blood calcium levels. For purposes herein, the name "parathyroid hormone (PTH)" is used herein, although all other names are contemplated. It is intended to encompass whole PTH with conservative amino acid substitutions that do not substantially alter its biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., MOLECULAR BIOLOGY OF THE GENE, 4th Edition, 1987, The Bejamin/Cummings Pub. Co., p.224). Whole PTH assay values may be obtained by measuring a sample with a Scantibodies Whole PTH Assay or a Scantibodies CAP Assay or a 3$^{rd}$ generation PTH Assay (both available from Scantibodies, Inc. (Santee, Calif.)) or a Nichols BioIntact PTH assay or an Immutopics Human Bioactive PTH assay. "Cyclase activating PTH" is a representative example of whole PTH.

As used herein, "parathyroid hormone (PTH) fragment" refers to a PTH fragment or derivative that counters the effect of whole PTH or otherwise lacks whole PTH activity in vivo. As also used herein, a PTH fragment may refer to a combination of one or more PTH fragments of variable lengths. It is intended to encompass PTH fragments with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al. MOLECULAR BIOLOGY OF THE GENE, 4th Edition, 1987, The Bejamin/Cummings Pub. co., p.224). "Cyclase inactive PTH" is a representative example of a PTH fragment.

As used herein, the terms "total PTH," "intact PTH" and "total intact PTH" are interchangeable and refer to the combination of whole PTH and PTH fragment levels, or an assay directed at measuring whole FM and PTH fragment levels.

As used herein the term "sample" refers to anything which is suspected of containing an analyze for which an analyze assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). Frequently, samples obtained for use in the present invention contain, or are suspected of containing, levels of PTH agonist and/or PTH antagonist that are detectable through methods described and contemplated herein.

As used herein, the term "protein matrix base" or "protein matrix" refers to the base material utilized to combine the one or more PTH components used in the present controls. Frequently, this base material is selected to prolong the active shelf-life of the presently contemplated controls. Although the base material may frequently be provided in liquid form used to combine the one or more PTH components, this base material is capable of being dried and stored for prolonged periods, together with the one or more PTH components. Serum comprises one representative protein matrix base material.

As used herein, the term "known concentration" refers to the concentration of one or more PTH components in a composition. Frequently, the one or more PTH components are measured into a known volume of base material to produce the presently contemplated known concentrations. On occasion, the one or more PTH components may be provided in a combination of whole PTH and PTH fragment at a predetermined ratio together measured into a known volume of base material. On occasion, this known concentration may be represented and/or measured in pmol/L or pmolmL, although other measurement scales and modes of measuring a component in a composition are contemplated.

As used herein, the term "predetermined ratio" refers to the ratio of whole PTH to PTH fragment components together in a composition. Those of skill in the art will recognize that the ratio of whole PTH to PTH fragment may also be inversely represented in a ratio of PTH fragment to whole PTH; in either presentation the information conveyed is the same. In the present controls the predetermined ratio may be provided via the combination of whole PTH and PTH fragment into one composition, each at known concentrations. When multiple controls are contemplated one or more different predetermined ratios may be provided in each of the control compositions. These different ratios are also each individually predetermined and frequently are provided over a selected ratio range.

As used herein, the term "physiological range" refers to a concentration range of a particular component in a subject. For example, a physiological range may refer to the concentration of a PTH component in a subject. A physiological range of an undefined PTH component can include a selection from a PTH fragment or whole PTH component In one aspect, the term physiological range may refer to whole PTH concentration ranges between about 0.7 pmol/L to about 3.9 pmol/l. See Woodhead, J. S., Clin. Biochem. 23, 17 (1990). Further, the physiological range is often about 1.0 pmol/L to about 4.0 pmol/L. Thus, a physiological range of whole PTH can be about 1 pmol/L, about 2 pmol/L, about 3 pmol/L, or about 4 pmol/L. Nevertheless, one of skill in the art understands that the measured physiological range of whole PTH can, on occasion, range outside of these concentrations. In addition, as an example, a physiological range of whole PTH may be about 3.9 pmol/L, thus the range of total PTH (accounting for one or more PTH fragment components) can be above the 3.9 pmol/L range. Moreover, a physiological range, as used herein, may also refer to the physiological concentration of a PTH component in a subject after exogenous administration of a PTH pharmaceutical agent.

As used herein, the term "PTH component" refers to whole PTH and/or PTH fragments. In addition, as used herein, PTH component may also refer to the combination of whole PTH and PTH fragments.

As used herein, the term "trial" refers to completion of a series of method steps. For example, as used herein, a trial might refer to assessing the accuracy of a PTH assay, however, it may further refer to correcting and/or interpreting the assay. The term "trial" as used herein also refers to the periodic regular checking and/or monitoring of a PTH assay in order to determine if the assay is generating consistently the same PTH values or ratio values for the same sample over a period of time. The use of trial analysis as described herein provides a useful method to detect assay drift and thus the patient can be protected from a misdiagnosis and a biotherapy that might arise there from. The term "trial" is not limited to specific method steps but it is intended to refer to a combination of one or more method steps described herein. It should be noted, however, that as used herein the term "trial" is different than the phrase "clinical trial" imparting a different meaning and significance.

The term "calibrating" is understood to mean compensating for measurement error and/or detecting sources of measurement error and/or detecting a drift in an assay or a change in value generation.

The term "multiplexed assay" is understood to mean an assay that can detect and/or measure multiple targets.

The term "target" is generally understood to mean any substance desired to be analyzed, including analyses, internal standards, internal controls, or any component of the assay reagent mixture.

The term "analyte" is understood to mean any substance suspected of being present in a sample.

The term "internal," when used in conjunction with standard or control, e.g. "internal standard" or "internal control," is understood to mean capable of being included in an assay reagent mixture or in any sample.

Thus, similarly, the phrase "internally calibrating" is understood to mean the use of internal standards and controls for calibrating assays.

The term "analyze of interest" refers to the analyze or analytes desired to be analyzed. The term "signal ligand" refers to a legend which is capable of being detected. A signal legend can be, for example, any substance having associated therewith a detectable label such as a fluorescently- or radioactively-tagged antibody or antigen.

The term "legend binding partner" refers to a legend capable of coupling with a target legend. According to the general method described above, the legend binding partner is typically conjugated to a particle. However, a "legend binding partner" can more generally be a legend capable of coupling with a target legend.

The term "target ligand" refers to a legend in (or put into) the reagent mixture or sample, which is capable of coupling with a legend binding partner. For example, an antibody associated with a particle and capable of coupling with an antigen in a sample is a "legend binding partner," while the antigen is a "target ligand." As another example, an antigen associated with a particle and capable of coupling with a signal legend is a "legend binding partner," while the signal legend is a "target ligand."

The term "tracer" refers to a signal legend that competes with a target legend for binding to a particular legend binding partner. For example, if a fluorescently-labeled antigen "A" and its unlabeled antigen "A" counterpart both compete for binding to a particular antibody associated with a particle, the fluorescently-labeled antigen is a "tracer," the unlabeled antigen is a "target ligand," and the antibody is a "legend binding partner."

The term "interfering factor" relates to any substance in the sample or reagent mixture which can interfere with the coupling of a legend binding partner and a target legend leading to an artificially low result.

B. Parathyroid Hormone Measurement Quality and Accuracy—Reagents and Controls

The present invention relates to methods of, and products for, measuring the quality, consistency and accuracy of hormone assays, particularly PTH assays, which can provide an assay system having minimal assay variation. Moreover, the present invention relates to a mode for calibrating, assessing or adjusting the quality and accuracy of hormone assays, particularly PTH assays. The present controls and kits are further useful for the detection of upward and/or downward shift in PTH assay values.

In one embodiment, PTH assay controls are provided comprising a composition having a known concentration of one or more components selected from the group consisting of: a) a whole PTH component having an amino acid sequence set forth in SEQ ID NO:1 ($PTH_{1-84}$), wherein the N-terminal amino acid residue of the PTH molecule must be intact; b) a PTH fragment component having an amino acid sequence set forth in SEQ ID NO:1 ($PTH_{1-84}$), wherein the N-terminal amino acid residue of the PTH fragment starts at any position spanning position 2 through position 33 of the $PTH_{1-84}$, the C-terminal amino acid residue of the PTH fragment ends at any position spanning position 35 through position 84 of the $PTH_{1-84}$; and the PTH fragment has a minimal length of three amino acid residues; and c) a total PTH component consisting of a combination of said whole PTH and said PTH fragment.

Frequently, the present controls are comprised of one or two or more of said whole PTH, PTH fragment or total PTH components combined in a protein matrix at a predetermined ratio of a parathyroid hormone assay control mixture. Further, the whole PTH component and/or the PTH fragment component are frequently provided in a purified or neat form in a soluble protein matrix. To maintain stability of the components in the protein matrix, frequently stabilizers and/or preservatives are included along with the PTH component. A variety of agents for accomplishing these purposes are well known. Without being bound by theory, agents and methods utilized to extend the shelf-life of the present controls should be selected to avoid adversely affecting the control compositions in terms of reactivity. One example of the presently contemplated matrices comprises a human serum (defibrinated plasma) product available from Scantibodies, Inc. (Santee, Calif.). Table 1 below provides the biochemical profile of a matrix of this type (See also http address: www.scantibodies.com/serumspec.pdf on the World Wide Web).

TABLE 1

| Biochemical Profile | |
|---|---|
| Albumin | 2.5-5.5 gm/dl |
| Globulin | 1.0-4.0 gm/dl |
| SGPT (ALT) | <90 μ/L |
| SGOT (AST) | <70 μ/L |
| GGT | <100 μ/L |
| Alk. Phos. | <120 μ/L |
| Calcium | <11.0 mg/dl |
| Phosphorus | <4.8 mg/dl |
| Sodium | 120-160 mEq/L |
| Potassium | <5.4 mEq/L |
| Chloride | 90-130 mEq/L |
| Cholesterol | >100 mg/dl - non-lipid stripped; <25 mg/dl - lipid stripped |
| Triglycerides | >60 mg/dl - non-lipid stripped; <20 mg/dl - lipid stripped |
| Iron | <500 μg/dl - non-charcoal stripped; <1000 μg/dl - charcoal stripped |
| HBsAg | Nonreactive at both the donor level and the pooled level |
| HIV-I/II Ab | Nonreactive at both the donor level and the pooled level. |
| HCV Ab | Nonreactive at the donor level. |
| STS | Nonreactive at the donor level. |

The presently described controls can exist in a liquid or dry form. Frequently, the present control are provided in a liquid or an otherwise reconstituted form for immediate use. Also frequently, when the controls are dried, they may be present in a lyophilized form. Lyophilization of the present control reagents may be accomplished by known methods to those of skill in the art. In one embodiment, reconstitution of dried or lyophilized control reagents is preferably carefully controlled such that the control composition includes a known concentration of one or more PTH components, and/or a predetermined ratio of PTH components. Reconstitution of the present controls is also preferable performed under conditions that permit the PTH components to remain intact.

In another embodiment, the whole PTH component and/or the PTH fragment component comprises chemically synthesized PTH peptides. Given the known amino acid composition of PTH and a variety of PTH fragments, chemical synthesis of whole PTH and/or a PTH fragment may be achieved by those skilled in the art. See, e.g., E. M. Evans and E. J. Wood, *DNA and Protein Synthesis* (Portland Press Ltd., 1987); R. Martin, Ed. *Protein Synthesis: Methods and Protocols. Methods in Molecular Biology*, Vol. 77 (Humana Press, 1998). Also frequently, the whole PTH component and/or the PTH fragment component are obtained as recombinant proteins. See, e.g., R. S. Tuan, Ed., *Recombinant Gene Expression Protocols: Methods in Molecular Biology*, Vol. 62 (Humana Press, 1997); R. S. Tuan, Ed., *Recombinant Protein Protocols: Methods in Molecular Biology*, Vol. 63 (Humana Press, 1997); Amstein HRV & Cox RA, *Protein Biosynthesis: In Focus* (IRL Press, Oxford, 1992).

In another embodiment, the whole PTH component and/or the PTH fragment component are frequently obtained from natural sources such as human serum, human plasma or via homogenization of human parathyroid gland. See, e.g., Deutscher, M., Ed., Guide to Protein Purification (Academic Press, 1990); Scopes, R., *Protein Purification: Principles and Practice* (Springer Verlag, 1982). One of skill in the art would appreciate the advantages, disadvantages and cost considerations of each of the above embodiments.

In another aspect, the present controls have extended shelf/storage lives. Therefore, in one embodiment, the shelf-life of the contemplated controls comprises a minimum of about 3 months. Frequently, the shelf-life of the present controls is between about 2 to about 3 years. On occasion, the present controls have a shelf-life between about 3 months to about 10 years. Also, less occasionally, the shelf-life of the present controls may range between about 1 month to about 9 months. Frequently, the present controls comprise a non-reconstituted PTH component that has a useful shelf life of at least three months at 4 degrees Celsius. Also frequently, the present controls comprise a non-reconstituted PTH component that has a useful shelf life of up to about 10 years at about 4 degrees Celsius. When the present control reagents are lyophilized they may be stored at room temperature for extended periods of time, but preferably in a refrigerated environment about or below 4 degrees Celsius.

In another aspect, the plurality of known concentrations are present in separate compositions with increasing concentrations from a nominal physiological amount. Generally, a physiological concentration of whole PTH ranges from about 0.7 pmol/L to about 3.9 pmol/L. However, the whole PTH component concentration may be provided in the present controls above or below this range. By way of non-limiting example, the presently contemplated control compositions appropriately include concentrations of a PTH component which normally exist in normal or disease patients, including concentrations of PTH components in patients receiving PTH-related therapeutics. For example, a PTH component can comprise a PTH fragment such as $PTH_{7-84}$ as a predominant PTH component. In one aspect, $PTH_{7-84}$ can be used in connection with $PTH_{1-84}$ forming a total PTH component as a suitable combination of PTH components for the present controls. On occasion, PTH fragments other than $PTH_{7-84}$ can be combined with $PTH_{1-84}$ to form a total PTH component. Thus, PTH components comprising PTH C-terminal, N-terminal and mid-terminal fragments are contemplated as useful components in the present controls.

Frequently, a whole PTH component concentration ranges between about 20% to about 80% of the control composition. On occasion, a whole PTH component concentration ranges from about 10% to about 90%. For example, a whole PTH component may fall within the following concentration ranges: about 5%, about 10%, about 20%, about 30%, about 40%, about 50%, about 60%, about 70%, about 80%, or about 90% of the total PTH component in the control composition. In a related aspect, the ratio of a whole PTH component concentration is a known and discrete concentration within the range between about 1% to about 99%.

Frequently, a PTH fragment component concentration ranges between about 20% to about 80% of the control composition. On occasion, a PTH fragment component concentration ranges from about 10% to about 90%. For example, a PTH fragment component may fall within the following concentration ranges: about 5%, about 10%, about 20%, about 30%, about 40%, about 50%, about 60%, about 70%, about 80%, or about 90% of the total PTH component in the control composition. In a related aspect, the ratio of the PTH fragment component concentration is a known and discrete concentration within the range between about 1% to about 99%.

As evidenced by the foregoing, the concentration of a PTH component in a control composition may be measured by known methods, including, for example, overall concentration within a protein matrix base material, or concentration versus the total PTH components in the sample.

Frequently, the ratio of a whole PTH component to a PTH fragment component in the present control compositions ranges between about 1% to about 99%. Moreover, on occasion the ratio of a whole PTH component to a PTH fragment component in the control is within a discrete range in the above ranges. For example, the ratio of a whole PTH component to a PTH fragment component may frequently be prepared within the following ranges: about 5%, about 10%, about 20%, about 30%, about 40%, about 50%, about 60%, about 70%, about 80%, about 90%, or about 100%. In a related aspect, the ratio of a whole PTH component to a PTH fragment component in the control is a known and discrete ratio within the disclosed range between about 1% to about 99%. Frequently, the ratio of a whole PTH component to a PTH fragment component in the present controls lies at a particular point or within a discreet physiological range. See, e.g., P. Gao, et al., *J. Bone Miner Res.* 16:4 605-615 (2001). In an important aspect of the present disclosure, the ratio of a whole PTH to a PTH fragment in a control composition may be predetermined and guided to lie at a particular point, or frequently within a discreet range. Without being bound by theory, preparation of control compositions having a particular ratio or ratio range of a whole PTH to a PTH fragment may be achieved through measurement and combination of particular amounts of whole PTH and PTH fragment in a composition.

In another embodiment, the ratio of the total PTH to a PTH fragment component in the control compositions ranges between about 1% to about 99%. On occasion the ratio of the total PTH component to a PTH fragment component in the control is within a discrete range in the above ranges. For example, the ratio of the total PTH component to a PTH fragment component may fall within the following ranges: about 5%, about 10%, about 20%, about 30%, about 40%, about 50%, about 60%, about 70%, about 80%, about 90%, or about 100%. In a related aspect, the ratio of the total PTH component to a PTH fragment component in the control is a known and discrete ratio within the disclosed range between about 1% to about 99%.

In yet another embodiment, the ratio of the total PTH component to a whole PTH component in the control compositions ranges between about 1% to about 99%. On occasion, the ratio of the total PTH component to a whole PTH component in the control is within a discrete range in the above ranges. For example, the ratio of the total PTH component to a whole PTH component may fall within the following ranges: about 5%, about 10%, about 20%, about 30%, about 40%, about 50%, about 60%, about 70%, about 80%, about 90%, or about 100%. In a related aspect, the ratio of the total PTH component to a whole PTH component in the control is a known and discrete ratio within the disclosed range between about 1% to about 99%.

In another embodiment, a parathyroid hormone (PTH) assay control is provided comprising one or more compositions, each having one of a plurality of concentrations of one or more, and frequently two or more components selected from the group consisting of: a) a whole PTH component having an amino acid sequence set forth in SEQ ID NO:1 ($PTH_{1-84}$), wherein the N-terminal amino acid residue of the PTH molecule must be intact; b) a PTH fragment component having an amino acid sequence set forth in SEQ ID NO:1 ($PTH_{1-84}$), wherein the N-terminal amino acid residue of the PTH fragment starts at any position spanning position 2 through position 33 of the $PTH_{1-84}$, the C-terminal amino acid residue of the PTH fragment ends at any position spanning position 35 through position 84 of the $PTH_{1-84}$; and the PTH fragment has a minimal length of three amino acid residues; and c) a total PTH component consisting of a combination of said whole PTH and said PTH fragment; wherein each of said one or more compositions comprise a mixture of said two or more components at a known ratio.

Frequently, any of the presently contemplated control compositions contains a known concentration of PTH components, and any one of the compositions further comprises one of a plurality of concentrations of the PTH components. For example, one of a plurality of compositions may contain a known concentration of either or both a whole PTH and a PTH fragment.

In another aspect, any of the presently contemplated control compositions frequently contain a known concentration of PTH components, and any one of the compositions comprises one of a plurality of known or predetermined ratios of the components. For example, one of a plurality of compositions may contain a known concentration of both a whole PTH and a PTH fragment. As the concentrations of each component may be known, the ratio of the components would be easily calculated. Without being bound by theory, ratios may be pre-calculated and prepared accordingly to a predetermined ratio.

In another embodiment, the present controls may be composed by spiking a matrix base with a PTH component comprising either whole PTH or PTH fragments, or a combination thereof. Chemically synthesized, recombinant, or native PTH components may be used in this process. The standards may be spiked such that the levels of the PTH component(s) therein lie approximately within a physiological range or at a point within a physiological range. Frequently, the PTH control composition is composed by compounding the one or more PTH components into a protein matrix.

C. Parathyroid Hormone Measurement Quality and Accuracy—Methods

In one embodiment, a method is provided to verify the accuracy of a PTH assay, comprising one or more trials of the following: a) evaluating a control of the type described above and herein utilizing a PTH assay having a specificity for the one or more of the PTH components within the control solution; b) determining the concentration(s) of the one or more components in the composition utilizing the assay of step a); and c) comparing the results obtained in step b) with the known concentration(s) of the one or more components in the control or comparing the values with those values obtained in the past in order to determine consistency over time of the assay performance. In an important aspect, the results of step c) may be utilized to accept, reject, modify or interpret PTH assay results obtained through the use of the PTH assay of step a) for non-control, test or subject samples.

Frequently, the contemplated methods further comprise generating a standard deviation of previously obtained control results in order to compare the recently obtained control values versus the known concentration results after one or more trials. Standard deviation or statistical information may be utilized to prepare criteria for accepting or rejecting a particular assay run of patient samples. Such methods are useful to interpret non-control samples having different PTH component concentrations and/or ratios than PTH component concentrations or ratios tested in control samples. On occasion, the standard deviation is utilized to modify and/or interpret PTH assay results for non-control samples. In a related aspect, step a) of the methods described above may comprise evaluating the control by multiple PTH assays having different specificities for the same or different PTH components; and the concentration(s) of the one or more components are determined by combining the results of the multiple PTH assays. In another example, one PTH assay may utilize reagents having different specificities of a PTH component (e.g., both the N-terminal and C-terminal regions of whole PTH). In another embodiment, the above methods are useful to adjust or evaluate the accuracy of a PTH assay. Other methods to adjust or evaluate the accuracy of a PTH based on results of an assay of control reagents are known in the art.

The present methods may be useful to provide information for risk assessment and risk management purposes. For example, results obtained through the present methods and the use of the present controls may be logged over time and occasionally revisited for risk management purposes. In a related example, a clinical lab that performs PTH component assessment may utilize the data obtained utilizing the present methods and compositions to ensure and demonstrate a heightened level of accuracy and consistency in their PTH assays.

In a further embodiment, a method is provided to verify the accuracy of a PTH assay, comprising one or more trials of the following: a) evaluating a control composition utilizing a PTH assay having a specificity for the one or more components; b) determining the concentration of one or both of the combination of components in the composition utilizing the assay of step a); and c) comparing the results obtained in step b) with the known concentration(s) and predetermined ratio of the combination of components. Frequently, the results of step c) may be utilized to modify or interpret PTH assay results obtained through the use of the PTH assay of step a) for non-control samples. In a related aspect, step a) may comprise evaluating the control by multiple PTH assays having different specificities; and the concentration(s) of the one or more components are determined by combining the results of the multiple PTH assays. In an infrequent embodiment, the present methods are useful to adjust the accuracy of a PTH assay (e.g., via changing the assigned values of calibrators). On occasion, the contemplated methods further comprise generating a standard deviation of the control results in order to assess newly obtained ratio control values from recent assays in order to provide criteria for accepting or rejecting the recent assay runs after one or more trials.

In yet another embodiment, a method is provided to verify the accuracy of a combination of PTH assays, comprising one or more trials of the following: a) evaluating the control of claim 2 utilizing a PTH assay having a specificity for whole PTH and determining the concentration of whole PTH in the control; b) evaluating a control composition utilizing a PTH assay that detects whole PTH and PTH fragments and determining the concentration of the whole PTH and PTH fragment in the control; c) determining the ratio of whole PTH to PTH fragments by comparing the concentration results of steps a) and b); and d) comparing the results obtained in step c) with the predetermined ratio of the control composition; wherein the results of step d) are utilized to modify or interpret PTH assay results obtained through the use of the PTH assays of steps a) and b) for non-control samples. Frequently, the present method further comprises generating a standard deviation of the results of step c) versus the predetermined ratio after one or more trials. Also frequently, each of the one or more trials entails the evaluation of a different control having a different predetermined ratio. In one aspect, the PTH assay of step a) may detect whole PTH having an intact N-terminal portion, and the PTH assay of step b) may detect total PTH levels.

In another embodiment, a method is provided to evaluate or adjust the accuracy of a PTH assay, comprising one or more trials of the following: a) utilizing a PTH assay to evaluate the one or more control compositions described above; b) determining the ratio and concentration of the two or more components in the one or more compositions; and c) comparing the control ratio and concentration results obtained in step b) with the known ratio and concentration of the two or more components in the one or more compositions; d) generating a standard deviation of the control results from past assay runs after one or more trials; and e) utilizing the standard deviation to evaluate and accept or reject PTH assay ratio and concentration results for non-control samples.

In a distinct embodiment, the present disclosure provides methods of detecting measurement errors in an assay, including multiplexed assays. In related embodiments, the method comprises adding internal controls for detecting omission of a sample or reagent to the reagent mixture. In further related embodiments, the method comprises adding internal controls for detecting interfering substances to the reagent mixture. In other related embodiments, the method comprises adding internal controls for alerting a user to possible high-dose hook effect to the reagent mixture. For example, high concentrations of whole PTH and PTH fragment components are combined in a control composition and assay results of the control compositions are then compared with the patient sample results.

It will be apparent to one of ordinary skill in the art that specific embodiments of the present invention may be directed to one, some or all of the above-indicated aspects as well as other aspects, and may encompass one, some or all of the above- and below-indicated embodiments as well as other embodiments. Thus, for example, a method according to the present invention may comprise adding internal controls to detect measurement errors.

Other embodiments are directed to methods for detecting errors that can occur as a result of the presence of interfering factors in the assay system. In immunoassays, interfering factors can affect coupling between the analyte and ligand binding partners. As a result, the detected signal corresponds to an amount of analyte that is lower than the actual amount of analyte in the sample and this will affect the ratio control value. According to this aspect of the present invention, internal controls can be used to identify whether interfering factors are present in the assay system.

The disclosed embodiments can also be modified to detect anomalies in addition to high-dose hook effect, and sample omission. For example, the matrix effect and rheumatoid factor are other sources of anomalies. Matrix or serum effects are sample-specific properties that interfere with the measurement of the test result. The matrix effect can be caused by an excess of particular bodily fluid constituents such as lipemia, bilirubinemia, hemoglobinemia, hemolytic, lipids, proteins, hemoglobin, immunologic, hormones, drugs, antigens, allergens, toxins, tumor markers, soluble cell molecules, and nucleic acid. These constituents can increase or decrease the measurement signal, causing an inaccurate result. Although the presently contemplated controls are not intended to detect specific sources of measurements error, their use enables the detection and monitoring of systematic problems in a PTH assay system, e.g., assay reagents or instrument measurement error. Detection and monitoring of systemic problems allows for the detection of specific sources of measurement error, e.g., sample anomalies.

D. Parathyroid Hormone Measurement Quality and Accuracy—Kits

In one embodiment, kits are provided comprising one or more control compositions of the present disclosure including instructions therefore. In one embodiment, a kit may comprise 1, 2, 3, 4, 5, 6, 7, 8, 9 or more discrete control compositions. Frequently, each discrete composition contains a known concentration and/or predetermined ratio of PTH components (i.e., assay calibrators) and may differ from the other compositions in the kit in terms of concentration and/or ratio to provide a range of potential control values. In one embodiment, kits may contain one or more means for storing PTH control compositions, each having a discrete known concentration or ratio of PTH components. In a further aspect, a diagnostic test kit may comprise a plurality of standards of known percentages of a whole PTH and/or a PTH fragment in a solution comprising a protein matrix.

In a further embodiment, the present kits may comprise labeled PTH components, e.g., acridities ester label. Other aspects may have other suitable labels. Numerous examples of detectable markers are know in the art, but preferable markers are those used in general PTH assay protocols. The presently contemplated kits may have other materials. Any suitable means to measure emitted light or spectral reading or radioactivity can be used as a part of the present kits and assay procedures. Other embodiments of the invention may have any suitable label on the PTH component and any suitable instrument for measuring the label, for example, a radio isotope label and an instrument that reads the radio isotope.

Another embodiment provides kits for the detection or quantitation of whole PTH and/or PTH fragments analytes. The kits can comprise one or more sets of PTH components, each set is distinguishable from other sets. In some embodiments, the kits comprise one or more batches of particles, each set being distinguishable from other batches, for example by its fluorescent signature. The particles are coupled to the PTH component. The particles, apart from the ligand binding partner, can be polymeric particles which range in size from 0.01 to 1000 micrometers in diameter. In one embodiment, the size ranges from 0.1-500 mum. In another embodiment the size ranges from 1-200 mum. In another embodiment the size ranges from 2-12 mum. The particles can be made of any of a variety of materials, including polymers (e.g., plastic, latex, etc.), metals, dyes, etc. Frequently, the particles are spherical in shape; however, particles of other shapes are contemplated. The shape of the particle can provide additional or alternative distinction parameters, which parameters can be discriminated by, for example, flow cytometry.

The kits can include sets of PTH components attached to particles for use as internal standards. On occasion, the kits can includes a set or sets of PTH components attached to particles for use as controls. On occasion, the kits can include sets of PTH components attached to particles for use as internal standards and a set or sets of particles for use as controls.

Without limitation, examples of means for determining and monitoring whole PTH levels in a subject comprise a variety of PTH assays indicated herein. A variety of means for determining and monitoring PTH component levels are known to those of skill in the art and may not have been specifically mentioned herein.

E. Parathyroid Hormone Fragments

In general, a PTH fragment of the present invention comprises a contiguous portion of human PTH having an amino acid sequence set forth in SEQ ID NO:1 ($PT_{1-84}$), or a nucleic acid encoding said portion of human PTH, and said PTH fragment has the following characteristics: a) the N-terminal amino acid residue of said PTH fragment starts at any position spanning position 2 through position 33 of said $PTH_{1-84}$; b) the C-terminal amino acid residue of said PTH fragment ends at any position spanning position 35 through position 84 of said $PTH_{1-84}$; and c) said PTH fragment has a minimal length of three amino acid residues. Preferably, the PTH fragment is in the form of a pharmaceutical composition, which pharmaceutical composition comprises an effective amount of the PTH fragment and a pharmaceutically acceptable carrier or excipient. Moreover, a variety of PTH fragments comprising N-terminal PTH fragments, C-terminal PTH fragments, and/or mid-terminal PTH fragments are contemplated herein.

In one embodiment the PTH fragments comprise a subset of serial cyclase inactive PTH. In one aspect the PTH fragments may be: $PTH_{3-84}$, $PTH_{4-84}$, $PTH_{5-84}$, $PTH_{6-84}$, $PTH_{7-84}$, $PTH_{8-84}$, $PTH_{9-84}$, $PTH_{10-84}$, and so forth.

In one embodiment, the N-terminal amino acid residue of the PTH fragment can start at any position spanning position 2 through position 33 of said $PTH_{1-84}$. For example, the N-terminal amino acid residue of the PTH fragment can start at position 2 of the $PTH_{1-84}$. The C-terminal amino acid residue of said PTH fragment can end at any position spanning position 35 through position 84 of said $PTH_{1-84}$. For example, the C-terminal amino acid residue of the PTH fragment can end at position 84 of the $PTH_{1-84}$.

In a specific embodiment, the PTH fragment is a protein or a peptide, or a nucleic acid encoding said protein or peptide, selected from the group consisting of $PTH_{2-84}$, $PTH_{3-84}$, $PTH_{4-84}$, $PTH_{5-84}$, $PTH_{6-84}$, $PTH_{7-84}$, $PTH_{8-84}$, $PTH_{9-84}$, $PTH_{10-84}$, $PTH_{11-84}$, $PTH_{12-84}$, $PTH_{13-84}$, $PTH_{14-84}$, $PTH_{15-84}$, $PTH_{16-84}$, $PTH_{17-84}$, $PTH_{18-84}$, $PTH_{19-84}$, $PTH_{20-84}$, $PTH_{21-84}$, $PTH_{22-84}$, $PTH_{23-84}$, $PTH_{24-84}$, $PTH_{25-84}$, $PTH_{26-84}$, $PTH_{27-84}$, $PTH_{28-84}$, $PTH_{29-84}$, $PTH_{30-84}$, $PTH_{31-84}$, $PTH_{32-84}$, and $PTH_{33-84}$. In another specific embodiment, the PTH fragment is a protein or a peptide, or a nucleic acid encoding said protein or peptide, selected from the group consisting of $PTH_{7-69}$, $PTH_{7-70}$, $PTH_{7-71}$, $PTH_{7-72}$, $PTH_{7-73}$, $PTH_{7-74}$, $PTH_{7-75}$, $PTH_{7-76}$, $PTH_{7-77}$, $PTH_{7-78}$, $PTH_{7-79}$, $PTH_{7-80}$, $PTH_{7-81}$, $PTH_{7-82}$, $PTH_{7-83}$ and $PTH_{7-84}$.

The PTH fragment can have any suitable length provided that it maintains its antagonizing activity. For example, the PTH fragment can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid residues.

Other features and advantages of the invention will be apparent from the following detailed description, and from the claims.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

What is claimed is:

1. A parathyroid hormone (PTH) assay control, comprising a composition having a known concentration of a whole PTH component mixed with a known concentration of a PTH fragment component, comprising:

a) a whole PTH component having an amino acid sequence set forth in SEQ ID NO:1 ($PTH_{1-84}$), wherein the N-terminal amino acid residue of the PTH molecule must be intact; and b) a PTH fragment component having an amino acid sequence set forth in SEQ ID NO:1 ($PTH_{1-84}$), wherein the N-terminal amino acid residue of the PTH fragment starts at any position spanning position 2 through position 33 of the $PTH_{1-84}$, the C-terminal amino acid residue of the PTH fragment ends at any position spanning position 35 through position 84 of the $PTH_{1-84}$; and the PTH fragment has a minimal length of four amino acid residues;

wherein the ratio of the whole PTH component to the PTH fragment component ranges between about 1% to about 99%, wherein said composition further comprises a protein matrix base, and wherein said assay control is lyophilized.

2. The PTH assay control of claim 1, wherein the composition comprises a total PTH component having the whole PTH component and the PTH fragment component combined in said protein matrix base at a predetermined ratio.

3. The PTH assay control of claim 1, wherein the whole PTH component and the PTH fragment component comprise chemically synthesized PTH peptides or recombinant protein.

4. The PTH assay control of claim 1, wherein the whole PTH component and the PTH fragment component are obtained from natural sources such as human serum, human plasma, or human parathyroid gland.

5. The PTH assay control of claim 4, wherein the whole PTH component and the PTH fragment component are purified prior to incorporation within the protein matrix.

6. The PTH assay control of claim 1, wherein the ratio of the whole PTH component to the PTH fragment component ranges between about 20% to about 80%.

7. A kit comprising one or more controls of claim 1 and instructions therefor.

8. The kit of claim 7, wherein the kit comprises two or more discrete controls, and each of the discrete controls comprises a composition having a different known concentration of the PTH components.

9. A kit comprising one or more controls of claim 2 and instructions therefor.

10. The kit of claim 9, wherein the kit comprises two or more discrete controls, and each of the discrete controls comprises a composition having a different ratio of PTH components.

11. The kit of claim 9, wherein each of the one or more controls comprises a composition having a different ratio of the whole PTH component versus the PTH fragment component.

12. The parathyroid hormone (PTH) assay control of claim 1, wherein the whole PTH component is $PTH_{1-84}$ and the PTH fragment component is $PTH_{7-84}$.

13. The parathyroid hormone (PTH) assay control of claim 1, wherein the whole PTH concentration ranges between about 0.7 pmol/L to about 3.9 pmol/l.

14. The parathyroid hormone (PTH) assay control of claim 1, wherein the PTH fragment component is selected from the group consisting of $PTH_{2-84}$, $PTH_{3-84}$, $PTH_{4-84}$, $PTH_{5-84}$, $PTH_{6-84}$, $PTH_{7-84}$, $PTH_{8-84}$, $PTH_{9-84}$, $PTH_{10-84}$, $PTH_{11-84}$, $PTH_{12-84}$, $PTH_{13-84}$, $PTH_{14-84}$, $PTH_{15-84}$, $PTH_{16-84}$, $PTH_{17-84}$, $PTH_{18-84}$, $PTH_{19-84}$, $PTH_{20-84}$, $PTH_{21-84}$, $PTH_{22-84}$, $PTH_{23-84}$, $PTH_{24-84}$, $PTH_{25-84}$, $PTH_{26-84}$, $PTH_{27-84}$, $PTH_{28-84}$, $PTH_{29-84}$, $PTH_{30-84}$, $PTH_{31-84}$, $PTH_{32-84}$, and $PTH_{33-84}$.

15. The parathyroid hormone (PTH) assay control of claim 1, wherein the PTH fragment component is selected from the group consisting of $PTH_{7-69}$,$PTH_{7-70}$, $PTH_{7-71}$,$PTH_{7-72}$, $PTH_{7-73}$,$PTH_{7-74}$,$PTH_{7-75}$,$PTH_{7-76}$,$PTH_{7-77}$, $PTH_{7-78}$, $PTH_{7-79}$,$PTH_{7-80}$,$PTH_{7-81}$,$PTH_{7-82}$,$PTH_{7-83}$, and $PTH_{7-84}$.

* * * * *

UNITED STATES PATENT AND TRADEMARK OFFICE

CERTIFICATE OF CORRECTION

PATENT NO. : 7,459,276 B2
APPLICATION NO. : 10/674294
DATED : December 2, 2008
INVENTOR(S) : Thomas L. Cantor et al.

It is certified that error appears in the above-identified patent and that said Letters Patent is hereby corrected as shown below:

Column 1, line 67, “under tang” should read --undertaking--.
Column 3, line 62, “acridities” should read --acridinium--.
Column 6, line 27, “FM” should read --PTH--.
Column 6, line 29, “an analyze for which an analyze” should read --an analyte for which an analyte--.
Column 6, line 65, “pmolmL” should read --pmol/mL--.
Column 7, line 51, “biotherapy” should read --mistherapy--.
Column 7, line 65, “analyses” should read --analytes--.
Column 8, line 10, ““analyze of interest” refers to the analyze” should read --“analyte of interest” refers to the analyte--.
Column 8, line 12, “legend” should read --ligand--.
Column 8, line 13, “legend” should read --ligand--.
Column 8, line 16, ““legend binding partner” refers to a legend” should read --“ligand binding partner” refers to a ligand--.
Column 8, line 17, “legend” should read --ligand--.
Column 8, line 18, “legend” should read --ligand--.
Column 8, line 19, “legend” should read --ligand--.
Column 8, line 20, “legend” should read --ligand--.
Column 8, line 21, “legend” should read --ligand--.
Column 8, line 22, “legend” should read --ligand--.
Column 8, line 24, “legend” should read --ligand--.
Column 8, line 26, “legend” should read --ligand--.
Column 8, line 28, “legend” should read --ligand--.
Column 8, line 29, ““legend binding partner,” while the signal legend” should read --“ligand biding partner,” while the signal ligand--.
Column 8, line 31, “legend” should read --ligand--.
Column 8, line 32, “legend for binding to a particular legend” should read --ligand for binding to a particular ligand--.
Column 8, line 37, “legend” should read --ligand--.
Column 8, line 41, “legend binding partner and a target legend” should read --ligand binding partner and a target ligand--.
Column 10, line 8, “Amstein” should read --Arnstein--.
Column 14, line 66, “hemolytic” should read --hemolysis--.
Column 14, line 67, “immunologic” should read --immunoglobin--.

UNITED STATES PATENT AND TRADEMARK OFFICE

CERTIFICATE OF CORRECTION

PATENT NO. : 7,459,276 B2
APPLICATION NO. : 10/674294
DATED : December 2, 2008
INVENTOR(S) : Thomas L. Cantor et al.

It is certified that error appears in the above-identified patent and that said Letters Patent is hereby corrected as shown below:

Column 15, line 29, “acridities” should read --acridinium--.

Signed and Sealed this

Twenty-sixth Day of May, 2009

JOHN DOLL
*Acting Director of the United States Patent and Trademark Office*